United States Patent [19]

Svacina et al.

[11] 4,325,254
[45] Apr. 20, 1982

[54] TEMPERATURE INDICATIVE HOTPACK

[75] Inventors: Lawrence M. Svacina, Denver; Donald N. James, Estes Park, both of Colo.

[73] Assignee: Staodynamics, Inc., Longmont, Colo.

[21] Appl. No.: 116,373

[22] Filed: Jan. 29, 1980

[51] Int. Cl.³ .................... G01K 1/14; G01K 11/12
[52] U.S. Cl. .................................. 73/356; 73/343 B; 116/216
[58] Field of Search .................. 73/356; 116/216; 128/736, 258; 150/2.1, 2.5

[56] References Cited

U.S. PATENT DOCUMENTS

| | | | |
|---|---|---|---|
| 1,535,536 | 4/1925 | MacDonald | 116/216 X |
| 2,285,776 | 6/1942 | MacCoy | 150/2.1 |
| 2,357,692 | 9/1944 | Saffady | 73/343 B |
| 2,460,215 | 1/1949 | Chase | 116/216 X |
| 2,799,167 | 7/1957 | Loconti | 73/356 |
| 2,826,073 | 3/1958 | Huyck et al. | 73/356 |
| 2,953,921 | 9/1960 | Muncheryan | 73/363.5 |
| 3,055,759 | 9/1962 | Busby et al. | 73/356 X |
| 3,696,675 | 10/1972 | Gilmour | 73/356 X |
| 3,769,932 | 11/1973 | Romito et al. | 73/356 X |
| 3,877,411 | 4/1975 | MacDonald | 73/356 X |
| 4,137,049 | 1/1979 | Couch et al. | 73/356 X |
| 4,137,769 | 2/1979 | Parker | 73/356 |
| 4,204,110 | 5/1980 | Smit et al. | 128/258 X |

FOREIGN PATENT DOCUMENTS

| | | | |
|---|---|---|---|
| 629448 | 4/1936 | Fed. Rep. of Germany | 150/2.5 |
| 1497623 | 10/1967 | France | 150/2.5 |

Primary Examiner—Daniel M. Yasich
Attorney, Agent, or Firm—O'Rourke & Harris

[57] ABSTRACT

A temperature indicative hotpack is disclosed. A temperature monitoring unit has an indicating portion and a sensing portion with the monitoring unit being mounted on one liquid permeable wall enclosing a heat retaining material so that the temperature of the heat retaining material is accurately determined by the sensing portion within the enclosure and displayed externally of the enclosure by means of the indicating portion so that the hotpack can be safely and effectively utilized.

11 Claims, 4 Drawing Figures

TEMPERATURE INDICATIVE HOTPACK

This invention relates to hotpacks and, more particularly, relates to temperature indicative hotpacks that may be safely and effectively utilized to apply moist heat to the human body after the hotpack has been heated by immersion in a hot liquid. In still greater particularity, this invention relates to a temperature indicative hotpack that includes an indication of the condition of the heat retaining material in the hotpack, including an indication of whether the hotpack is ready for use.

BACKGROUND OF THE INVENTION

Temperature measurement is important in many fields. This is especially true in the medical field where heat is often utilized, including for example, for sterilization of equipment and for patient therapy. Many physicians and physical therapists prefer the use of moist heat to other forms of heat for patient therapy, and to effect this end, hotpacks have herefore been developed and utilized in medical treatment such as, for example, in the treatment of arthritis and for muscle therapy.

Hotpacks conventionally include a cover having one or more pockets, or cells, contained therein, each of which contain a heat retaining material. The hotpacks are placed in a heated liquid, such as hot water, until the heat retaining material within the cells absorb sufficient heated water to raise the temperature of the hotpack to a desired level. One widely used heat retaining material is clay, such as bentonite, since bentonite, in addition to retaining heat from the absorbed liquid, also expands upon absorption of the liquid to fill the cells in which it is enclosed.

A major problem in the use of hotpacks has been the problem of determining when the heat retaining material in the hotpack has reached a temperature level sufficient to be effectively utilized to impart moist heat to a patient. In the past, this determination has largely been made on a subjective basis. That is, the hotpacks were heated for a time period which was thought to raise the temperature of the heat retaining material to the desired level. Thus, due to environmental and other factors, a user could not be certain that the hotpack was even close to the desired temperature. Often a number of hotpacks were treated in a single container of liquid. Unless the hotpacks were all placed into the container at the same time, however, it was difficult, if not impossible, to distinguish how long a particular hotpack had been exposed to the heating process. It was therefore exceedingly difficult with prior art hotpacks to insure safe and effective use at least without utilizing other cumbersome and/or elaborate systems.

Devices are known which provide an indication of a predetermined temperature having been reached. One such device is shown in U.S. Pat. No. 2,826,073. That device is a sterilization indicator which includes strips of paper or similar materials which are placed in packs of medical instruments. A thermosensitive indicating material on the indicator inserted in the packs indicates that the materials to be sterilized have been exposed to steam for a period of time sufficient to attain sterilization. Thus, this device measures the temperature of the steam or liquid which is used to sterilize instruments, but does not measure the internal temperature of the instruments.

A device for determining the internal temperature of an object is disclosed in U.S. Pat. No. 4,137,769. That device employs a model of the object for which it is desired that the internal temperature be known. The model is placed in the heating medium along with the object. The model includes a thermochromic material known in the prior art which changes color at different temperatures. The thermochromic material may be in the shape of numbers to change colors and become visible at a temperature indicated by a particular number, but measurement of the internal temperature of objects is restricted to measurement only of the internal temperature of the model and then is only valid if the objects and model are subjected to the same heat for the same period of time.

Other known devices, such as heat thermometers, which might be thrust into the center of a material whose temperature is to be measured, are impractical for use with hotpacks in that they would destroy the integrity of the cover which must remain sufficiently intact to retain the heat retaining material (but yet must be liquid permeable to allow liquid to pass into and out of the enclosure having the heat retaining material therein).

SUMMARY OF THE INVENTION

This invention relates to a hotpack and, more particularly, relates to a temperature indicative hotpack that is particularly suitable for applying moist heat to a human body. The hotpack includes a liquid permeable cover defining an enclosed space containing a heat retaining material. A temperature monitor is mounted on the cover and includes a sensor that extends into the enclosed space and therefore into contact with the heat retaining material. The temperature monitor also includes an indicator that provides a visual indication externally of the cover that the heat retaining material has attained a predetermined temperature due to heating of the material, normally due to subjecting the material to a hot liquid for a period of time.

In the disclosed embodiment of the invention, a porous cloth-like material is utilized as the cover to form an enclosure having bentonite therein as the heat retaining material that absorbs liquid during the heating process. A thermometer indicator, or dot, has portions which change color at a predetermined temperature to indicate the state of the heat retaining material and, more particularly, to indicate when the hotpack is ready for use.

OBJECTS OF THE INVENTION

It is therefore an object of this invention to provide an improved hotpack.

It is a further object of this invention to provide a temperature indicative hotpack.

It is yet another object of this invention to provide a hotpack with a temperature monitor for sensing the internal temperature of heat retaining material retained within the outer cover of the hotpack and to indicate the condition of the heat retaining material externally of the cover.

It is still another object of this invention to provide a hotpack with a temperature monitor to indicate when the heat retaining material of the hotpack has reached a predetermined temperature and that the hotpack is ready for use.

It is a further object of this invention to provide a hot-pack with a temperature monitor whereby the condition of the hotpack with respect to temperature may be quickly ascertained to enhance safe and effective use of the hotpack.

With these and other objects in view, which will become apparent to one skilled in the art as the description proceeds, this invention resides in the novel construction, combination and arrangement of parts substantially as hereinafter described and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figure 1:
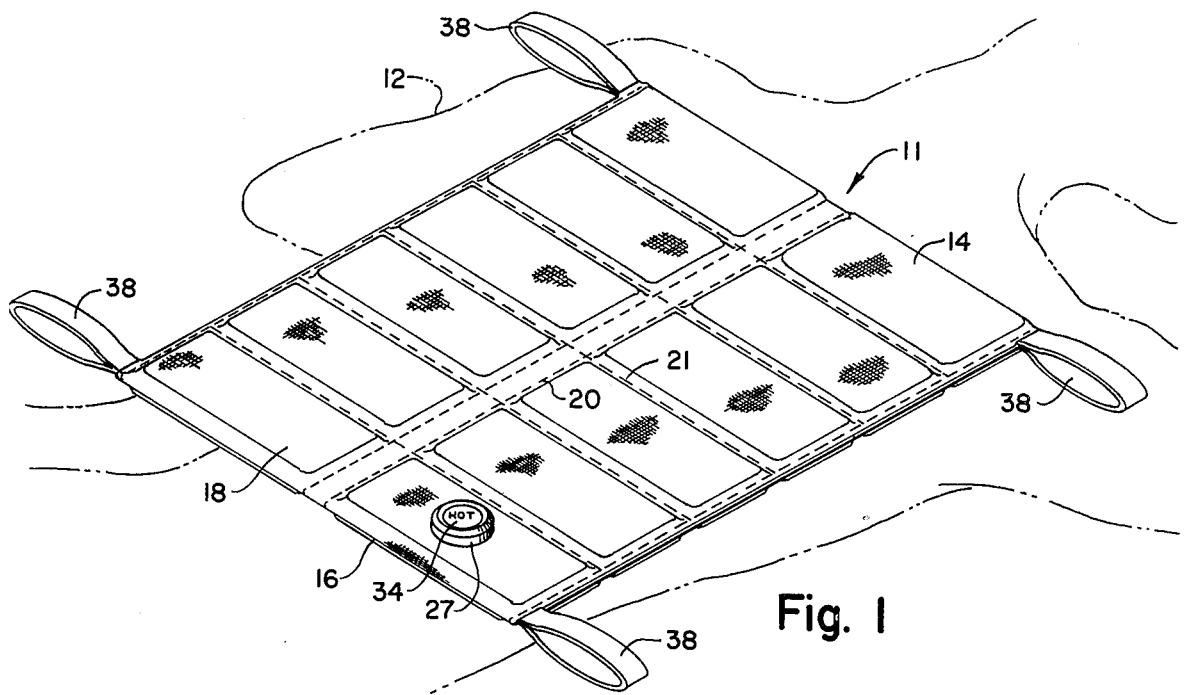
FIG. 1 is a perspective view of the temperature indicative hotpack of this invention, which hotpack may be applied to a human body.

Turning now to the drawings, FIG. 1 shows a hotpack, generally designated as 11, which is utilized to apply moist heat to a body, such as, for example, a human body 12.

Figure 4:
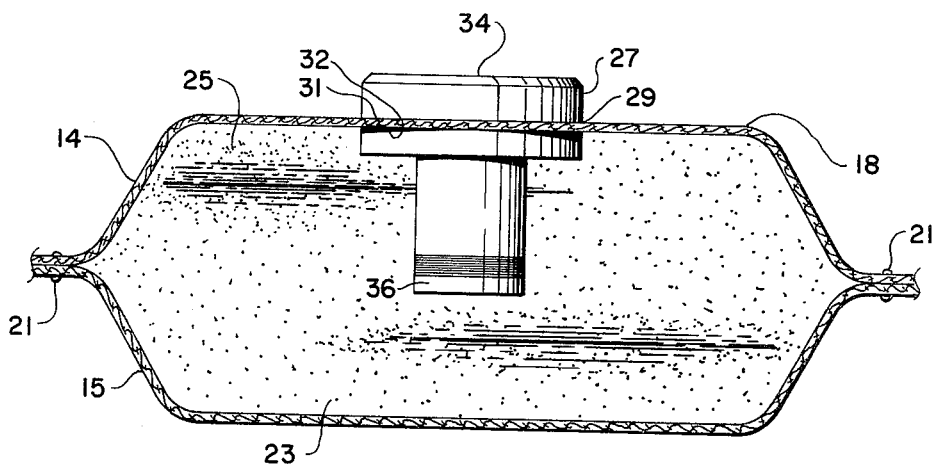
FIG. 4 is a side sectional view of a hotpack cell illustrating the temperature monitor in place therein.

Hotpack 11 is formed by adjacent sheets 14 and 15, as best shown in FIG. 4, of porous, or liquid permeable, material, such as cotton duct, for example, which sheets are joined, as by sewing, for example, at the outer edges 16 (the sheets may also be folded to avoid the need for sewing the edges whenever possible) to form an outer cover 18. In addition, as shown in FIG. 1, the sheets forming the outer cover 18 may be joined along juncture lines 20 and 21 (normal to one another and extending from side to side of the sheet) to form pockets 23, which pockets are essentially enclosed spaces for receiving heat retaining material 25 therein, as best shown in FIG. 4.

The outer cover 18 is chosen so that when the hotpack is immersed in a hot liquid, such as water, the liquid passes through the cover and into contact with the heat retaining material, which may be, for example, clay, and preferably bentonite. The heat retaining material is chosen so as to be raised in temperature when subjected to a heated medium, such as hot water, and then slowly release the heat when brought to a medium of lower temperature, as is well known.

A temperature monitor, or dot, 27 is mounted on cover 18 by means of a collar securing portion 29 having shoulders 31 and 32 engaging opposite sides of sheet 14. As shown, monitor 27 includes an externally visible indicating portion, or face, 34 and a sensing portion 36 which extends away from the surface and well into the heat retaining material 25, as again best shown in FIG. 4. A plurality of loops 38 are attached to each of the corners of cover 18 for facilitating handling of the hotpack, particularly when heated.

Figure 2:
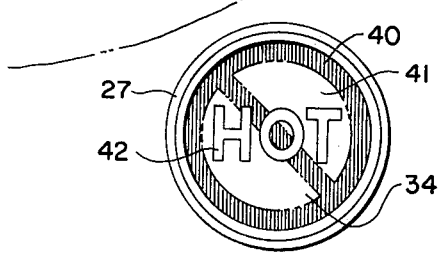
FIG. 2 is a top view of the temperature monitor shown in FIG. 1 with the indicator indicating that the hotpack is "NOT HOT" and therefore not ready for use.
Figure 3:
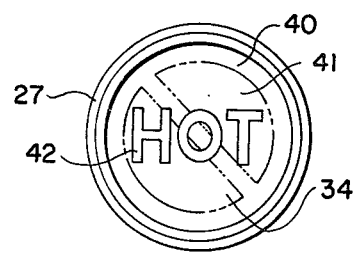
FIG. 3 is a top view of the temperature monitor similar to that of FIG. 2 except that the indicator is indicating that the hotpack is "HOT" and therefore ready for use.

While only one temperature monitor 27 is shown, it is to be appreciated that a plurality could be utilized, if desired. Referring to FIG. 2, face 34 of the thermometer monitoring unit 27 is shown, for illustration purposes, having a changeable background area 40, a constant background area 41, and a constant foreground area 42. These areas may be different colors, so as to portray a "NOT HOT" condition (FIG. 2) or a "HOT" condition (FIG. 3). The indicia and/or particular scheme for indicating a particular condition may, of course, be varied as desired so long as the condition correctly portrays the condition being sensed by sensing portion 36 of the temperature monitoring unit. For the illustration of FIGS. 2 and 3, sensing portion 36 of the monitor is preferably a two condition sensor with a rapid change at a predetermined temperature, which sensors are well known to the art. Temperature monitor 27 may include a metal casing, and preferably has a plastic face for indicating the then prevailing condition of the heat retaining material externally of the cover.

MODE OF OPERATION

Referring to FIG. 1, hotpack 11 may be placed on a human body 12 after the hotpack has been heated sufficiently so that the heat retaining material 25 in enclosed spaces 23 has been heated to a predetermined temperature sufficient to cause the temperature monitor to indicate that the hotpack is ready for use. This indication takes the form of the word "HOT" clearly visible on face 34 in the illustration of FIG. 3.

Until the hotpack is ready for use, the not ready indication of the hotpack is indicated on face 34 of the thermometer monitor unit. As shown in the illustration of FIG. 2, the "NOT HOT" condition is shown by the word HOT circled with a slanted line thru the word which is achieved by background areas 40 and 41 being of different colors with the foreground area 42 (i.e., HOT) being of yet another color (or white) as shown in FIGS. 1 and 3. When the temperature of the heat retaining material reaches the predetermined temperature, background area 40 changes color so that it is the same color as background area 41. The word "HOT" has not changed color, however, and is now clearly visible indicating to the user that the temperature of the heat retaining material has attained the predetermined temperature. Of course, other designs may be utilized for face 34 of the thermometer monitoring unit such as, for example, background areas 40 and 41 could remain the same color and the word "HOT" could change color upon reaching the predetermined temperature. Additionally, other words and/or different indicia other than "HOT", such as "GO" or "READY", could also be used on face 34.

As shown best in FIG. 4, thermometer unit 27 is attached to sheet 14 of cover 18 by means of collar 29 so that the sensor 36 is located near the center of enclosed space 23 in thermal contact with the clay 25 therein. Thermometer unit 27 may be attached, however, in any conventional fashion to cover 18. For use as a two condition indicator, sensor unit 36 has a rapid change so that the indicating face, or dot, is reversible such that when the temperature of the heat retaining material drops below the predetermined temperature, the face will change state and indicate the "NOT HOT" condition (as illustrated in FIG. 2), and when the heat retaining material is again raised to a temperature above the predetermined temperature, the face will change state and indicate a "HOT" condition (as illustrated in FIG. 3). The predetermined temperature found best suited for use with hotpacks is about 70° C.

As is known in the art, when the hotpack is immersed in hot water until ready for use, the heat retaining material (bentonite) absorbs water and swells to fill the pockets formed by cover 18. When sufficiently hot, as shown by temperature monitor 27, the hotpack is brought to a position adjacent to the body to apply moist heat to the body with the heat of the hotpack being slowly dissipated during this period until it is no longer effective (at which time the condition "NOT HOT" is shown by temperature monitor 27).

While not specifically shown in FIG. 1, it is to be understood that conventional hotpack treatment recommends that the hotpack not be applied directly to a human body. Instead a layer of towels or other such materials are normally placed between the hotpack and the human body, and, in addition, the hotpack may be wrapped in towels to help insulate the hotpack so that it will retain heat for a longer period of time.

As can be appreciated from the foregoing, this invention provides an improved hotpack that includes temperature indications to facilitate safe and effective use.

What is claimed is:

1. A temperature indicative hotpack for applying moist heat to a body, said hotpack comprising:
   a liquid permeable cover having an enclosed space therein;
   a heat retaining material within said enclosed space formed by said liquid permeable cover, said material being capable of absorbing hot liquid to heat the same, and said cover being of a material to retain said heat retaining material when said cover is both dry and wet;
   at least one temperature monitor having a collar portion for securing said monitor to said liquid permeable cover with said monitor being retained on said cover when said cover is both wet and dry, said temperature monitor having an elongated temperature sensing portion within said enclosed space formed by said liquid permeable cover and in thermal contact with said heat retaining material therein, and said temperature monitor also having an indicating portion responsive to the temperature of said heat retaining material sensed by said sensing portion, said indicating portion including visually discernable indicia at least a portion of which assumes one state when the temperature of said heat retaining material is below a predetermined temperature to indicate a not sufficiently heated condition, and a second state when the temperature of said heat retaining material is above said predetermined temperature to indicate a sufficiently heated condition.

2. The hotpack of claim 1 wherein said cover is formed of cotton duct material.

3. The hotpack of claim 1 wherein said heat retaining material is bentonite.

4. The hotpack of claim 1 wherein said at least a part of said indicia of said indicating portion of said temperature monitor changes color to indicate said one state and said second state.

5. The hotpack of claim 4 wherein said indicia includes the word HOT, and wherein said color changeable part of said indicia is at least part of the background so that in said one state an indication of NOT HOT is provided and in said second state an indication of HOT is provided.

6. A temperature indicative hotpack for applying moist heat to a body, said hotpack comprising:
   a liquid permeable cover having an enclosed space therein;
   a heat retaining material contained in said enclosed space, said heat retaining material being capable of absorbing hot liquid upon exposure thereto through said liquid permeable cover, and said cover being of a material to retain said heat retaining material when said cover is both dry and wet; and
   at least one temperature monitor having an indicating portion, a securing portion for securing said monitor to said cover so that said indicating portion is externally viewable thereat and with shoulders of said securing portion on opposite sides of said cover retaining said monitor secured to said cover when said cover is both dry and wet, and an elongated sensing portion within said enclosed space so as to be in contact with said heat retaining material therein whereby an external indication is provided by the temperature monitor with respect to the temperature of said heat retaining material within said cover, said indicating portion including visually discernable contrast means that assumes a first state indicative of a sufficiently heated condition when said heat retaining means of said hotpack is above a predetermined temperature, and assumes a second state different from said first state and indicative of a not sufficiently heated condition when said heat retaining material of said hotpack is below said predetermined temperature.

7. The hotpack of claim 6 wherein said retaining material includes bentonite.

8. The hotpack of claim 6 wherein said external indication provided by said indicating portion of said temperature monitor includes at least two discernable areas at least one of which is varied depending upon the temperature of said heat retaining material sensed by said sensing portion of sensing monitor.

9. The hotpack of claim 6 wherein said liquid permeable cover is formed of a cloth-like material.

10. The hotpack of claim 6 wherein said contrast means includes the word HOT and a changeable background to indicate NOT HOT when said heat retaining material is sensed to be at a temperature below said predetermined temperature.

11. A hotpack according to claim 10 wherein said predetermined temperature is about 70° C.

* * * * *